United States Patent [19]

Thompson et al.

[11] Patent Number: 4,847,247

[45] Date of Patent: Jul. 11, 1989

[54] PENICILLIN DERIVATIVES AS ANTI-INFLAMMATORY AND ANTIDEGENERATIVE AGENTS

[75] Inventors: Kevan R. Thompson, Westfield; Paul E. Finke, Milltown; James B. Doherty, New Milford, all of N.J.

[73] Assignee: Merck & Co., Inc., Rahway, N.J.

[21] Appl. No.: 922,312

[22] Filed: Oct. 16, 1986

Related U.S. Application Data

[63] Continuation of Ser. No. 635,700, Jul. 30, 1984, abandoned.

[51] Int. Cl.$^4$ .................. C07D 499/00; A61K 31/425
[52] U.S. Cl. .................... 514/194; 514/192; 514/195; 540/310
[58] Field of Search ................ 540/310; 514/192, 195, 514/194

[56] References Cited

U.S. PATENT DOCUMENTS

| 3,546,211 | 12/1970 | Base | 260/239 |
| 4,035,359 | 7/1977 | Christensen | 424/263 |
| 4,287,181 | 9/1981 | Kellogg | 424/114 |
| 4,493,839 | 1/1985 | Doherty et al. | 424/263 |
| 4,711,886 | 12/1987 | Finke et al. | 540/310 |

FOREIGN PATENT DOCUMENTS

| 0124081 | 7/1984 | European Pat. Off. |
| 1454587 | 11/1976 | United Kingdom |
| 2053220 | 4/1979 | United Kingdom |

Primary Examiner—Nicholas S. Rizzo
Attorney, Agent, or Firm—Theresa Y. Cheng; Michael C. Sudol

[57] ABSTRACT

Derivatives of Penicillin, their sulfoxides and sulfones are found to be potent elastase inhibitors and thereby useful anti-inflammatory/antidegenerative agents.

9 Claims, No Drawings

PENICILLIN DERIVATIVES AS ANTI-INFLAMMATORY AND ANTIDEGENERATIVE AGENTS

This application is a continuation of U.S. patent application Ser. No. 635,700 filed on July 30, 1984 and now abandoned.

BACKGROUND OF THE INVENTION

We have found that derivatives of penicillin, their sulfoxides and sulfones are potent elastase inhibitors. They are therefore useful anti-inflammatory and antidegenerative agents.

Proteases from granulocytes and macrophages have been reported to be responsible for the chronic tissue destruction mechanisms associated with inflammation, including rheumatoid arthritis and emphysema. Accordingly, specific and selective inhibitors of these proteases are candidates for potent anti-inflammatory agents useful in the treatment of inflammatory conditions that cause connective tissue destruction, e.g. rheumatoid arthritis, emphysema, bronchial inflammation, osteoarthritis, spondylitis, lupus, psoriasis and acute respiratory distress syndrome.

The role of proteases from granulocytes, leukocytes or macrophages are related to a rapid series of events which occurs during the progression of an inflammatory condition:

(1) There is a rapid production of prostaglandins (PG) and related compounds synthesized from arachidonic acid. This PG synthesis has been shown to be inhibited by aspirin-related nonsteroidal anti-inflammatory agents including indomethacin and phenylbutazone. There is some evidence that protease inhibitors prevent PG production;

(2) There is also a change in vascular permeability which causes a leakage of fluid into the inflamed site and the resulting edema is generally used as a marker for measuring the degree of inflammation. This process has been found to be induced by the proteolytic or peptide cleaving activity of proteases, especially those contained in the granulocyte, and can therefore be controlled by various synthetic protease inhibitors, for example, N-acyl benzisothiazolones and the respective 1,1-dioxides. Morris Zimmerman et al., *J. Biol. Chem.*, 255, 9848 (1980); and B. Ashe et al., *J. Biol. Chem.*, 256, 11603 (1981). (3) p There is an appearance and/or presence of lymphoid cells, especially macrophages and polymorphonuclear leukocytes (PMN). It has been known that a variety of proteases are released from the macrophages and PMN, further indicating that the proteases do play an important role in inflammation.

In general, proteases are an important family enzymes within the peptide bond cleaving enzymes whose members are essential to a variety of normal biological activities, such as digestion, formation and dissolution of blood clots, the formation of active forms of hormones, the immune reaction to foreign cells and organisms, etc., and in pathological conditions such as the degradation of structural proteins at the articular cartilage/pannus junction in rheumatoid arthritis etc.

Elastase is one of the proteases. It is an enzyme capable of hydrolyzing the connective tissue component elastin, a property not contained by the bulk of the proteases present in mammals. It acts on a protein's nonterminal bonds which are adjacent to an aliphatic amino acid. Neutrophil elastase is of particular interest because it has the broadest spectrum of activity against natural connective tissue substrates. In particular, the elastase of the granulocyte is important because, as described above, granulocytes participate in acute inflammation and in acute exacerbation of chronic forms of inflammation which characterize many clinically important inflammatory diseases.

Proteases may be inactivated by inhibitors which block the active site of the enzyme by binding tightly thereto. Naturally occurring protease inhibitors form part of the control or defense mechanisms that are crucial to the well-being of an organism. Without these control mechanisms, the proteases would destroy any protein within reach. The naturally occurring enzyme inhibitors have been shown to have appropriate configurations which allow them to bind tightly to the enzyme. This configuration is part of the reason that inhibitors bind to the enzyme so tightly (see Stroud, "A Family of Protein-Cutting Proteins" *Sci. Am.* July 1974, pp. 74–88). For example, one of the natural inhibitors, $\alpha_1$-Antitrypsin, is a glycoprotein contained in human serum that has a wide inhibitory spectrum covering, among other enzymes, elastase both from the pancreas and the PMN. This inhibitor is hydrolyzed by the proteases to form a stable acyl enzyme in which the active site is no longer available. Marked reduction in serum $\alpha_1$-antitrypsin, either genetic or due to oxidants, has been associated with pulmonary emphysema which is a disease characterized by a progressive loss of lung elasticity and resulting respiratory difficulty. It has been reported that this loss of lung elasticity is caused by the progressive, uncontrolled proteolysis or destruction of the structure of lung tissue by proteases such as elastase released from leukocytes. J. C. Powers, *TIBS*, 211 (1976).

Rheumatoid arthritis is characterized by a progressive destruction of articular cartilage both on the free surface bordering the joint space and at the erosion front built up by synovial tissue toward the cartilage. This destruction process, in turn, is attributed to the protein-cutting enzyme elastase which is a neutral protease present in human granulocytes. This conclusion has been supported by the following observations:

(1) Recent histochemical investigations showed the accumulation of granulocytes at the cartilage/pannus junction in rheumatoid arthritis; and (2) a recent investigation of mechanical behavior of cartilage in response to attack by purified elastase demonstrated the direct participation of granulocyte enzymes, especially elastase, in rheumatoid cartilage destruction. H. Menninger et al., in *Biological Functions of Proteinases*, H. Holzer and H. Tschesche, eds. Springer-Verlag, Berlin, Heidelberg, New York, 1979, pp. 196–206.

Accordingly, an object of this invention is to discover new protease inhibitors, especially elastase inhibitors, useful for controlling tissue damage and various inflammatory or degenerative conditions mediated by proteases particularly elastase.

Another object of the present invention is to provide pharmaceutical compositions for administering the active substituted penicillin derivatives, their sulfoxides and sulfones as protease inhibitors.

Still a further object of this invention is to provide a method of controlling inflammatory conditions by administering a sufficient amount of one or more of the active, substituted penicillin derivatives, their sulfoxides and sulfones in a mammalian species in need of such treatment.

DETAILED DESCRIPTION OF THE INVENTION

A: Scope of the invention

This invention relates to penicillin deriva their sulfoxides and sulfones as potent elastase inhibitors useful in the prevention, control and treatment of inflammatory conditions especially arthritis and emphysema.

Penicillin free acids are well known antibiotics which have been described in numerous Patents, for example, U.S. Pat. Nos. 4,260,598; 4,234,579; 4,316,842; 4,035,359; Great Britain Pat. Nos. 2053-220; 2077-728; Belgium Pat. Nos. 885-812; 819-594; 882-027; 832-173; European Pat. Nos. 27-010; 13-617; 41-047; 50-805; Netherland Pat. No. 8100-209; and Japanese Pat. Nos. 3090-286; and 0101-380.

The generic formula of the compounds of the present invention is represented as follows:

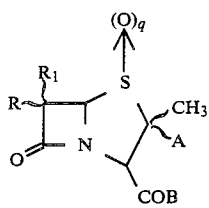
(I)

wherein
q is 0, 1 or 2; preferably q is 1 or 2; and more preferably, q is 2.

A is
(a) hydrogen;
(b) $C_{1-6}$ alkyl especially methyl;
(c) $CH_2OR_a$ wherein $R_a$ represents $C_{1-6}$-alkyl or H;
(d) $CH_2X$ wherein X represents halo especially Cl or F;
(e) $CH_2OCOR_a$;
(f) $CH_2Q$ wherein Q represents

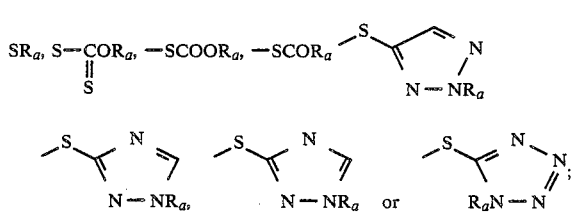

and
(g) $CH_2NHR_a$.

Preferably, A is
(a) $CH_2OCOR_a$ especially

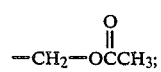

(b) $-CH_3$;
(c) $CH_2OR_a$ where $R_a$ represents $C_{1-3}$alkyl especially methyl or isopropyl;
(d) $CH_2Cl$; or
(e) hydrogen;
more preferably, A is $CH_3$ or $CH_2OCOCH_3$;

$R_1$ is (a) is nitrogen bonded group including $R'NR_a$— wherein $R'$ and $R_a$ are defined below;
(b) hydrogen;
(c) hydroxy;
(d) mercapto;
(e) substituted oxy;
(f) substituted thio;
(g) hydrocarbyl or substituted hydrocarbyl group;
(h) cyano;
(i) carbonyl or thiocarbonyl containing substituents bonded by said carbonyl or thiocarbonyl radical;
(j) halo;
(k) phosphono or a substituted phosphono group; or
(l) hydroxyalkyl especially hydroxy-$C_{1-6}$alkyl such as $CH_3CH(OH)$—;
(m) alkoxycarbonyloxyalkyl especially $C_{1-6}$alkoxycarbonyloxy $C_{1-6}$alkyl such as $CH_3CH(OCOOt-Bu)$—;
(n) benzoxycarbonyloxy-$C_{1-6}$alkyl, e.g., $CH_3CH(OCOOCH_2C_6H_5)$—;
(o) phenoxycarbonyloxy-$C_{1-6}$alkyl such as $CH_3CH(OCOOC_6H_5)$—; or
(p) alkoxycarbonylalkyl.

When $R_1$ is $R'NR_a$—, $R'$ represents a substituted or unsubstituted aliphatic, aromatic or heterocyclic, aralipahatic or heterocyclylaliphatic carboxylic acid radical or a carbothioic acid radical such as the acyl radicals of the known cephalosporins and penicillins. These acyl radicals can be represented by the general formula

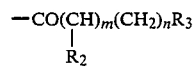

wherein $R_2$ is loweralkyl, haloloweralkyl, aryl, aralkyl and substituted derivatives of these groups. m and n represent 0–4 and $R_3$ represents $R''$ or $ZR_d$, which are also defined below.

One group of the acyl radicals, i.e., when m and n are both 0 and $R_3$ is $R''$, can be represented by the general formula

wherein $R''$ is:
(a) straight or branched chain alkyl having from 1 to 20 carbon atoms especially methyl, ethyl, isopropyl, t-butyl, pentyl or hexyl;
(b) aryl having from 6 to 10 carbon atoms especially phenyl, substituted phenyl or naphthalene;
(c) cycloalkyl having from 3 to 8 carbon atoms especially cyclopentyl, or cyclohexyl;
(d) alkenyl having from 2 to 20 carbon atoms especially $C_{2-6}$alkenyl such as vinyl, allyl, or butenyl;
(e) cycloalkenyl having from 5 to 8 carbon atoms especialy cyclopentenyl or cyclohexenyl;
(f) alkynyl having from 2 to 20 carbon atoms especially $C_{2-6}$alkynyl for example, ethynyl, propynyl or hexynyl;
(g) alkoxy having from 1 to 10 carbon atoms especially $C_{1-3}$ alkoxy such as methoxy, ethoxy or n-propoxy or i-propoxy;
aralkyl, alkaryl, aralkenyl, aralkynyl, alkenylaryl or alkynylaryl wherein alkyl, aryl, alkenyl and alkynyl are as previously defined;

(i) monoheteroaryl, di- or polyheteroaryl, or fused heteroaryl containing from 1 to 3 of any one or more of the heteroatoms N, S or O in each heteroaryl ring thereof, for example, pyridyl, pyrryl, thienyl, isothiazolyl, imidazolyl, pyrazinyl, pyrimidyl quinolyl, isoquinolyl, benzothienyl, isobenzofuryl pyrazolyl, indolyl, purinyl, carbozolyl, isoxazolyl and the like;

(j) heteroarylalkyl such as 2-pyridylmethyl, 2-thienylmethyl and 3-isothiazolylethyl;

(k) hydrogen; or (l) halo $C_{1-6}$alkyl especially $CF_3$ and $CCl_3$;

The above groups (a)-(b) and (i) can be unsubstituted or can be substituted by radicals such as alkyl, alkoxy, halo such as fluoro, chloro, bromo or iodo, cyano, carboxy, sulfoamino, carbamoyl, amino or alkyl sulfonyl, azido, amino, substituted amino such as monoalkylamino and dialkylamino, haloalkyl, carboxyalkyl, carbamoylalkyl, N-substituted carbamoylalkyl, guanidino, N-substituted guanidino, guanidinoalkyl, and the like. Representative examples of such acyl groups that might be mentioned are those wherein R'' is methoxy, ethoxy, benzyl, p-hydroxybenzyl, 3- or 4-nitrobenzyl, p-aminobenzyl, o-aminobenzyl, m-aminobenzyl, o-sulfobenzyl, p-carboxymethylbenzyl, p-carbamoylmethylbenzyl, m-fluorobenzyl, m-bromobenzyl, p-chlorobenzyl, p-methoxybenzyl, p-aminomethylbenzyl, hydrogen, methyl, ethyl, cyanomethyl, 2-pentenyl, n-amyl, n-heptyl, phenethyl, difluoromethyl, trifluoromethyl, dichloromethyl, dibromoethyl, 1-(3-methylimidazolyl)methyl, 2- or 3-(5-carboxymethylthienyl)methyl, 2- or 3-(4-carbamoylthienyl)methyl, 2- or 3-(5-methylthienyl)methyl, 2- or 3-(5-methoxythienyl)methyl, 2- or 3-(4-chlorothienyl)methyl, 2- or 3-(5-sulfothienyl)methyl, 2- or 3-(5-carboxythienyl)methyl, 3-(1,2,5-thiadiazolyl)methyl, 3-(4-methoxy-1,2,5-thiadiazolyl)methyl, 2-furylmethyl, 2-(5-nitrofuryl)methyl, 3-furylmethyl, 2-thienylmethyl, and tetrazolylmethyl. The term "sulfo" represents substituted or unsubstituted mercapto or thio, sulfinyl and sulfonyl.

The acyl group can also be a radical of the formula

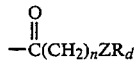

wherein n is 0-4, Z represents oxygen, sulfur or nitrogen, and $R_d$ is R'' with the proviso that $R_d$ cannot be alkoxy. Representative members of the substituent

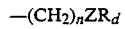

are allylthiomethyl, allylaminomethyl, phenylthiomethyl, butylmercaptomethyl, α-chlorocrotylmercaptomethyl, phenoxymethyl, phenylaminomethyl, phenoxyethyl, phenoxybutyl, phenoxybenzyl, diphenoxymethyl, dimethylmethoxymethyl, dimethylbutoxymethyl, dimethylphenoxymethyl, 4-guanidinophenoxymethyl, 4-pyridylthiomethyl, p-(carboxymethyl)-phenoxymethyl, p-(carboxymethyl)phenylthiomethyl, 2-thiazolylthiomethyl, p-(sulfo)phenoxymethyl, p-(sulfo)phenylthiomethyl, p-(carboxy)phenoxymethyl, p-(carboxy)phenylthiomethyl, p-(carboxymethyl)phenoxymethyl, p-carboxymethyl)phenylthiomethyl, 2-pyrimidinylthiomethyl, phenethylthiomethyl, 1-(5,6,7,8-tetrahydronaphthyl)oxomethyl, 6,8-bis(methylthio)octanoyl.

Furthermore, the acyl group can be a radical of the formula

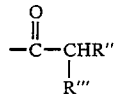

wherein R'' is defined as above and R''' is a radical such as amino hydroxy, azido, carba , guanidino, alkanoyloxy, halo, sulfamino, tetrazolyl, sulfo, carboxy, carbalkoxy, and the like. Representative members of the substituent

are α-aminobenzy, α-amino-2-thienyl, α-methylaminobenzyl, α-amino-*-methyl-mercaptopropyl, α-amino-3 or 4-chlorobenzyl, α-amino-3 or 4-hydroxybenzyl, α-amino-2,4dichlorobenzyl, α-amino-3,4-dichlorobenzyl, D(—)-α-hydroxybenzyl, α-carboxybenzyl, α-amino-3-thienyl, α-amino-2-thienyl, 2-thienyl, D(—)-α-amino-3-chloro-4-hydroxybenzyl, D(—)-α-amino-3-thienyl, 1-aminocyclohexyl, α-(5-tetrazolyl)benzyl, α-sulfaminobenzyl, α-sulfamino-3-thienyl, α-(N-methylsulfamino)-benzyl, D(—)-α-guanidino -2-thienyl, D(—)-α-guanidinobenzyl, α-guanylureidobenzyl, α-hydroxybenzyl, α-azidobenzyl, α-fluorobenzyl, 4-(5-methoxy-,3-oxadiazolyl)aminomethyl, 4-(5-methoxy-1,3-oxadiazolyl)hydroxymethyl, 4-(5-methoxy-1,3-oxadiazolyl)-carboxymethyl, 4-(5-methoxy-1,3-sulfadiazolyl)-aminomethyl, 4-(5-methoxy-1,3-sulfadiazolyl)-hydroxymethyl, 4-(5-methoxy-1,3-sulfadiazolyl)-carboxymethyl, 2-(5-chlorothienyl)-aminomethyl, 2-(5-chlorothienyl)hydroxymethyl, 2-(5-chlorothienyl)-carboxymethyl, 3-(1,2-thiazolyl)aminomethyl, 3-(1,2-thiazolyl)hydroxymethyl, 3-(1,2-thiazolyl)-carboxymethyl, 2-(1,4-thiazolyl)aminomethyl, 2-(1,4-thiazolyl)-hydroxymethyl, 2-(1,4-thiazolyl)-carboxymethyl, 2-benzothienylaminomethyl, 2-benzothienylhydroxymethyl, 2-benzothienylcarboxymethyl, α-sulfobenzyl, and α-phosphonobenzyl. Finally, there can be two groups attached to the amino function for example, phathalimido; and R'—CO—N-$R_a$—.

Alternatively, the group

can be an unsubstituted or substituted alkyl or aryl sulfonamido group wherein R' is $R_2SO_2$ such as $C_{1-6}$alkyl-$SO_2$; $CF_3SO_2$; $C_6H_5SO_2$; or $C_6H_5CH_2SO_2$. For example, phenylsulfonamido, ethylsulfonamido, trifluoromethane sulfonamido, benzylsulfonamido, 2,5-dimethylsulfonamido, 4-chlorophenylsulfonamido, 4-methoxyphenylsulfonamido, or an unsubstituted or substituted alkyl or aryl sulfonylalkylamino group wherein R' is $R_aSO_2R_a$, e.g., $CH_3SO_2CH(CH_3)$—, or benzyl or substituted phenyl $SO_2R_a$, e.g., (p—F—$C_6H_4$)$SO_2CH_2$—, $C_6H_5SO_2CH_2$, and the like.

Preferably, R' is:

(1) hydrogen;

(2)

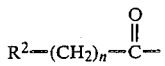

where
R² represents:
 (a) hydrogen;
 (b) methyl or substituted methyl such as trifluoromethyl, cyanomethyl or methoxymethyl;
 (c) thienyl;
 (d) phenyl; or
 (e) mono- and disubstituted phenyl and thienyl wherein the substituents are selected from the group consisting of chloro, bromo, fluoro, nitro, loweralkyl, and loweralkoxy;
n is 0 or 1;
(3)

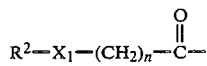

where
X₁ is oxygen or sulfur;
R² and n are as previously defined;
(4) NH₂—C(=NH)NH—CH(C₆H₅)CO;
(5) R₂SO₂—;
(6) (R₂O)₂(P=O)—; or
(7) R₂(C=S).
Even more preferably, R' is

,

R² being selected from the group consisting of:
 (1) trifluoromethyl;
 (2) methyl;
 (3) methoxy;
 (4) hydrogen;
 (5) benzyl;
 (6) phenyl;
 (7) 2-thienylmethyl;
 (8) phenylthiomethyl;
 (9) phenoxymethyl;
 (10) benzyloxy;
 (11) NCCH₂SCH₂; or
 (12) R₂SO₂—.

The oxy or thio substituent represented by R₁ can be a substituted hydroxy or mercapto group such as —XR₁' wherein X is oxygen or sulfur and R₁' is a hydrocarbyl group, preferably a straight or branched loweralkyl group of 1–6 carbon atoms, a straight or branched chain loweralkenyl or loweralkynyl group of 3–6 carbon atoms, a monocyclic aryl group such as phenyl, furyl, pyrryl and pyridyl, or an aralkyl group such as benzyl. These alkyl, alkenyl, alkynyl, aryl or aralkyl groups can be substituted with groups such as hydroxy, halo, nitro, amino, carboxy, thio, and the like. Other specific substituents represented by R₁ that might be mentioned are groups of the formula —OAc, —SAc, —SO₃H, —OSO₂R₂, SO₂NH₂, —OCD₃, —SO₂R₂, —SO₂NR₃R₄, —OCOOR₂, —SOR₂, —OCOSR₂, —O-CONR₃R₄, and the like wherein Ac represents an acyl group such as a formyl or lower-alkanoyl, R₃ and R₄ independently represent hydrogen, or R₂, and R₂ represents loweralkyl, haloloweralkyl, aryl, aralkyl and substituted derivatives of such groups, e.g., p—CH₃—C₆H₄—, CF₃, CH₃ and benzyl.

When R₁ is hydrocarbyl it can be straight or branched loweralkyl, straight or branched lower-alkenyl, loweralkynyl, aralkyl, cycloalkyl, a monocyclic aryl group, or a monocyclic heterocyclic group which can also be substituted with one or more groups such as halo, hydroxy, alkoxy, amino, nitro, sulfonyl, sulfamoyl, acyloxy, carbamoyloxy, carboxy, carboxamido and N-substituted carboxamido. Representative examples of such groups are C₁₋₆ alkyl such as methyl, trifluoromethyl, ethyl, n-propyl, isopropyl, t-butyl; C₂₋₆ alkenyl especially allyl, α-butenyl; C₂₋₆ alkynyl such as ethynyl and methylethynyl; loweraralkyl such as benzyl, p-methoxybenzyl, phenethyl; phenyl, p-aminophenyl; cyclopropyl, cyclopentyl and 4-hydroxycyclohexyl;

R₁ may also represent cyano or a group of the genera formula

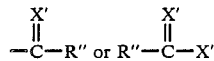

wherein X' is oxygen, —NR_a, sulfur, and R'' is hydrogen, halo, hydroxy, mercapto, amino, substituted amino, alkyl, aryl, aralkyl, aralkoxy such as benzyloxy, alkoxy or aryloxy such as phenoxy, pyrroloxy, furyloxy, and thienyloxy, alkylthio or arylthio. Examples of these substituents are —COOH, —CSSH, —COR₂, —COOR₂, —COSR₂, —CSSR₂, —CONH₂, —CSNH₂, —CSR₂, —CONHR₂, —CSNH, —CONR₃R₄,

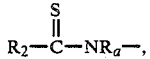

and —CSNR₃R₄, wherein R₃ and R₄ represent hydrogen or R₂;

Furthermore, R₁ represents a nitrogen bonded group such as amino, substituted amino groups, nitro, azido, nitroso, isocyanato, isothiocyanato and hydroxyamino. Specific examples of nitrogen bonded groups that might be mentioned are —N₃, —NH₂, —NHR_a, NR_aR₃, wherein R_a represents a straight or branched chain loweralkyl group of 1 to 6 carbon atoms, R₃ represents R_a or hydrogen, and n represents the integer 1 or 2.

Finally, the substituent R₁ represents phosphono or a metal or ammonium salt thereof, or a substituted phosphono group of the formula:

where Y' and Z' are the same or different and represent —OR₂, —NR₃R₄,

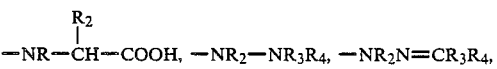

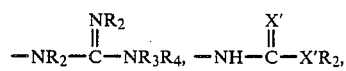

-continued

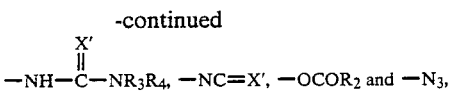

where $R_3$ and $R_4$ represent hydrogen, hydrocarbyl, alkoxy or an acyl radical, and $X'$ represents oxygen or sulfur.

Preferably, $R_1$ is
(1) $R'NR_a$ wherein $R_a$ is H or $C_{1-6}$ alkyl and $R'$ is
  (a) hydrogen;
  (b) $CF_3CO$;
  (c) $CF_3OCO$
  $R_2SO_2$ wherein $R_2$ is phenyl or substituted phenyl, benzyl or substituted benzyl, $C_{1-6}$alkyl, H or $CF_3$ especially —$SO_2$phenyl or substituted phenyl, e.g., p—$CH_3$—$C_6H_4SO_2$—;
  (e) $R_2CO$;
  (f) $R_2O(CO)$;
  (g) $(R_2O)_2P(O)$—;
  (h) $R_2$ especially benzyl or substituted benzyl;
  (i) $R_2(C=S)$—;
(2) $C_{1-6}$alkoxycarbonyloxy$C_{1-6}$alkyl;
(3) benzoxycarbonyloxy$C_{1-6}$alkyl;
(4) hydroxyalkyl especially hydroxy$C_{1-6}$alkyl;
(5) $OR_1'$ where $R_1'$ is
  (a) $C_{1-6}$alkyl;
  (b) phenyl or substituted phenyl;
  (c) benzyl or substituted benzyl;
  (d) —$COR_2'$ wherein $R_2'$ represents H, $R_2$, or $C_{1-6}$alkylamino such as $CH_3NH$—, or $C_2H_5NH$—;
  (e) $COOR_2$;
(6) $SR_1$;
(7) hydrogen;
(8) $C_{1-6}$alkyl;
(9) $C_{1-6}$ alkoxycarbonyl $C_{1-6}$ alkyl;
(10) phenoxycarbonyloxy $C_{1-6}$ alkyl;
(11) benzylaminocarbonyloxy$C_{1-6}$alkyl e.g., —$CH_2OCONHCH_2C_6H_5$ and

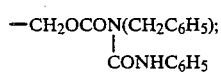

or
(12) $R'NR_b$—wherein $R_b$ is $C_{1-6}$alkyl.
(13) OH;
(14) CN;
(15) halo;
(16) —$O(CO)CH_2OR_2$;
(17) —$COOR_2$;
(18) —$CH_2SR_2$;
(19) phthalimido;
$R_1$ and R joined together forming

wherein $R_c$ is H, $C_{1-6}$alkyl or halo and $R_d$ is CN, $COR_a$, $C_6H_5(CO)$—; or substituted $C_6H_5(CO)$.

Even more preferably, $R_1$ is
(1) $R'NR_a$ where $R'$ represents:
  (a) $CH_3CO$—;
  (b) $CF_3CO$—;
  (c) HCO—;
  (d) methoxycarbonyl; or (e) P—$CH_3C_6H_5SO_2$13
(2) $R'NCH_3$—;
(3) $C_{1-3}$alkyl;
(4) —$CH_2C_6H_5$;
(5) $OR_1'$ where $R_1'$ is
  (a) $C_{1-6}$ alkyl especially methyl, ethyl, n-propyl;
  (b) —$C_6H_5$;
  (c) —$CH_2C_6H_5$; or
  (d)

where $R_2'$ represents hydrogen, $C_{1-6}$alkyl, phenyl, or substituted phenyl, benzyl or substituted benzyl such as p-nitrobenzyl, or $C_{1-6}$alkylamino such as $CH_3NH$—, $C_2H_5NH$—;
  (e) (p-$CH_3$—$C_6H_4$)—$SO_2$—;
(6) Cl or F;
(7) —$SO_2R_2$ wherein $R_2$ is benzyl or substituted benzyl;
(8) $CH_3OR_3'$ or $CH_3CH(OR_3)$ wherein $R_3'$ is —$COOCH_2C_6H_5$, —$OCOCH_2$—(p—$NO_2$—$C_6H_5$), —$CONHCH_2C_6H_5$ or —$CON(CH_2C_6H_5)(CO)NHCH_2C_6H_5$;
(9) H;
(10)

(11)

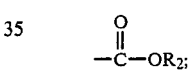

(12)

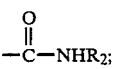

(13) —$CH_2SO_2R_2$; or
(14) —$CH_2SR_2$.

B of Formula (I) above represents $OB_1$, or $NB_2B_3$ wherein $B_1$ and $B_2$ independently are:
  (a) straight or branched chain alkyl having from 1 to 20 carbon atoms, ethyl, isopropyl, t-butyl, pentyl or hexyl;
  (b) aryl having from 6 to 10 carbon atoms;
  (c) cycloalkyl having from 3 to 8 carbon atoms;
  (d) alkenyl having from 2 to 20 carbon atoms;
  (e) cycloalkenyl having from 5 to 8 carbon atoms;
  (f) alkynyl having from 2 to 20 carbon atoms;
  (g) alkoxy having from 1 to 10 carbon atoms;
  (h) aralkyl, alkaryl, aralkenyl, aralkynyl, alkenylaryl or alkynylaryl wherein alkyl, aryl, alkenyl and alkynyl are as previously defined;
  (i) loweralkenylalkyl;
  (j) alkanoylalkyl;
  (k) alkanoyloxyalkyl;
  (l) alkoxyalkyl;
  (m) alkanoyloxy;
  (n) a heterocyclic group including heterocyclic alkyl or heterocyclic alkenyl;
  (o) benzoxycarbonyl;
  (p) —$CH_2COOH$;

(q) —CH₂COOC₁₋₆alkyl;
(r) —CH₂COObenzyl;

The above groups (a)-(n) can be unsubstituted or can be substituted by radicals such as alkyl, hydroxy, alkoxy, halo, nitro, mercapto, amino, monoalkylamino or dialkylamino, cyano, carboxy, sulfoamino, carbamoyl, —COOH, —COOC₁₋₆alkyl, carbamoyloxy, sulfonyl, sulfinyl, sulfamoyl, azido, carboxamido or N-alkyl carboxamido; and B₃ is hydrogen or B₁; and B₂ and B₃ may join together and form part of the heterocyclic group

e.g.:

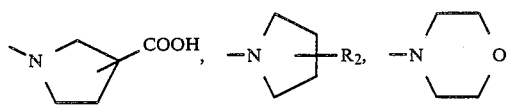

or the like. Representative examples of such groups are C₁₋₆alkyl especially methyl, ethyl or t-butyl, allyl, 3-butenyl, methoxyethyl, benzyl, p-carbomethoxybenzyl, m-carbomethoxybenzyl, p-sulfonylbenzyl, m-fluorobenzyl, (p-t-butoxycarbonyl)benzyl, o,p-dinitrobenzyl, o,p-dichlorobenzyl, p-methylbenzyl, p-methoxybenzyl, o-methylthiobenzyl, benzhydryl, CH₂CH₂CH₂COOCH₃, —CH₂COOC₂H₅, and the like.

Preferably B₁ and B₂ independently are substituted or unsubstituted
(1) aralkyl;
(2) aryl;
(3) straight or branched loweralkyl;
(4) CH₂COOH;
(5) CH₂COOC₁₋₆alkyl;
(6) alkanoyloxyloweralkyl;
(7) alkanoylloweralkyl;
(8) alkoxyloweralkyl;
(9) haloalkyl; or
(10) CH₂COObenzyl; or B₃ is H or B₁; and B₂ and B₃ may join together and form part of the heterocyclic group as defined previously;

Even more preferably, B₁ and B₂ independently are substituted or unsubstituted
(1) benzyl or substituted benzyl;
(2) C₁₋₄alkyl especially methyl, ethyl, isopropyl and t-butyl;
(3) —CH₂COOC₁₋₄alkyl;
(4) —CH₂COOH;
(5) CH₂COObenzyl;
(6) alkanoyloxymethyl;
(7) alkanoylmethyl; or
(8) halo C₁₋₄alkyl especially CF₃CH₂; or
(9) benzoxycarbonyl;

B₃ is H or B₁; and B₂ and B₃ may join together and form part of the heterocyclic group selected from a group consisting of:

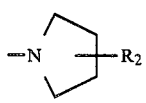

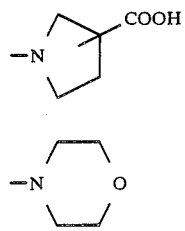

R is
(a) H;
(b) halo;
(c) OR₂; or
(d) C₁₋₆alkyl.

Preferably, R is
(a) H;
(b) —OC₁₋₆alkyl;
(c) C₁₋₂alkyl; or
(d) Cl or F.

More preferably, R is
(a) H;
(b) CH₃ or C₂H₅; or
(c) OCH₃

B: Preparation of the compounds within the scope of the present invention

The compounds of formula (I) where B is OH are known penicillin acids and where B is other than —OH, the compounds are esters or amides which can be prepared from the corresponding acids according to conventional methods of esterification or amidation. For example, (1) A compound of formula (I) (wherein B is OH) is treated with a lower alkanol, a substituted or unsubstituted benzyl alcohol, or a substituted or unsubstituted benzhydrol (diphenylmethanol) in the presence of a catalyst such as sulfuric acid, hydrochloric acid and any one or a combination of the acid illustrated below in Table I.

TABLE I

| Catalysts for Esterification |
|---|
| (1) Hydrochloric acid or hydrobromic acid |
| (2) Sulfuric acid |
| (3) C₁₋₃alkanoic acid e.g. acetic acid |
| (4) Phosphoric acid |
| (5) Trifluoroacetic acid or anhydride |
| (6) Trichloroacetic acid |
| (7) p-Toluenesulfonic acid or other arylsulfonic acids |
| (8) Acidic ion-exchange resins with calcium sulfate |
| (9) Polymer-protected aluminum chloride, e.g., a complex between anhydrous aluminum chloride and polystyrene-divinyl benzene copolymer diphenylphosphitepyridine |
| (10) A Lewis acid such as boron trifluoride |
| (11) Aromatic sulfonylchloride-pyridine, e.g., p-toluenesulfonylchloride |
| (12) triphenylphosphine ditriflate |
| (13) dicyclohexylcarbodiimide (DCCD) |
| (14) β-trichloromethyl-β-pro-piolactone |
| (15) N,N'—carbonyldimidazole |
| (16) triphenylphosphinediethylazodicarbonylate |
| (17) 6-chlorobenzensulfonyloxybenzotriazole |
| (18) 1-methyl-2-halopyridinium iodide-tertiary amine (e.g., triethylamine). | at from about 0° to about 150° C. with or without refluxing until the esterification is substantially complete. Optionally, a (2) A compound of formula (I) is converted to an acid halide such as acid chloride or bromide via treatment with a halogenating agent such as thionyl chloride, phosphorus penta- or oxychloride followed by reaction with an appropriate alcohol; or amine; and (3) Other methods such as alkylation of carboxylate salts (e.g., $K^+$, $Na^+$, $Ca^{++}$, $Ag^+$, $Cu^+$, tetralkylammonium $R_4N^+$, and $Hg^{++}$ salts) of formula (I) with alkyl halides, for example, benzylchloride, benzyhydryl chloride; reaction with alkyl isoureas; treatment with diazomethane or diazophenylmethane ($C_6H_5CHN_2$); alcoholysis of anhydride derived from the cephalosporin acid corresponding to formula (I); transesterification with t-butyl esters or i-propenyl acetate and the like may also be used. These methods are disclosed in Saul Patai, editor, *The Chemistry of Functional Groups*, Supplement B, *The Chemistry of Acid Derivatives*, pp. 411–436, John Wiley & Sons, Chichester-New York-Brisbane-Toronto, 1979, and are incorporated herein by reference.

C. Utility of the compounds within the scope of the invention

This invention also relates to a method of treatment for patients (or mammalian animals raised in the dairy, meat, or fur industries or as pets) suffering from inflammation, degeneration or pain. More specifically, it relates to a method of treatment involving the administration of a compound of formula (I) as the active constituent.

For the treatment of inflammation and pain a compound of formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as horses, cattle, sheep, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets containing the active ingredient in admixture with non-toxic pharmaceutically acceptable excipients may also be manufactured by known methods. The excipients used may be for example, (1) inert diluents such as calcium carbonate, sodium carbonate, lactose, calcium phosphate or sodium phosphate; (2) granulating and disintegrating agents such as corn starch, or alginic acid; (3) binding agents such as starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coat the techniques described in the U.S. Pat. Nos. 4,256,108; 4,160,452; and 4,265,874 to form osmotic therapeutic tablets for controlled release.

In some cases, formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, for example peanut oil, liquid paraffin, or olive oil.

Aqueous suspensions normally contain the active materials in admixture with excipients suitable for the manufacture of aqueous suspensions. Such excipients may be (1) suspending agents such as sodium carboxymethylcellulose, methylcellulose, hydroxypropylmethylcellulose, sodium alginate, polyvinylpyrrolidone, gum tragacanth and gum acacia;

(2) dispersing or wetting agents which may be
  (a) a naturally-occurring phosphatide such as lecithin,
  (b) a condensation product of an alkylene oxide with a fatty acid, for example, polyoxyethylene stearate,
  (c) a condensation product of ethylene oxide with a long chain aliphatic alcohol, for example, heptadecaethyleneoxycetanol,
  (d) a condensation product of ethylene oxide with a partial ester derived from a fatty acid and a hexitol such as polyoxyethylene sorbitol monooleate, or
  (e) a condensation product of ethylene oxide with a partial ester derived from a fatty acid and a hexitol anhydride, for example polyoxyethylene sorbitan monooleate.

The aqueous suspensions may also contain one or preservatives, for example, ethyl or n-propyl p-hydroxybenzoate; one or more coloring agents; one or more flavoring agents; and one or more sweetening agents such as sucrose or saccharin.

Oily suspension may be formulated by suspe the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an antioxidant such as ascorbic acid.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example, those sweetening, flavoring and coloring agents described above may also be present.

The pharmaceutical compositions of the invention may also be in the form of oil-in-water emulsions. The oily phase may be a vegetable oil such as olive oil or arachis oils, or a mineral oil such as liquid paraffin or a mixture thereof. Suitable emulsifying agents may be (1) naturally-occurring gums such as gum acacia and gum tragacanth, (2) naturally-occurring phosphatides such as soy bean and lecithin, (3) esters or partial esters derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

A compound of (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the anti-inflammatory agents are employed.

Dosage levels of the order from about 1 mg to about 100 mg per kilogram of body weight per day are useful in the treatment of the above-indicated conditions (from about 50 mg to about 5 gms. per patient per day). For example, inflammation is effectively treated and antipyretic and analgesic activity manifested by the administration from about 2.5 to about 75 mg of the compound per kilogram of body weight per day (about 75 mg to about 3.75 gms per patient per day).

The amount of active ingredient that may be combined with the carrier materials to produce a single dosage form will vary depending upon the host treated and the particular mode of administration. For example, a formulation intended for the oral administration of humans may contain from 5 mg to 5 gm of active agent compounded with an appropriate and convenient amount of carrier material which may vary from about 5 to about 95 percent of the total composition. Dosage unit forms will generally contain between from about 25 mg to about 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

D. Biological evidence in support of utility of the invention

It has been found that the compounds of Formula (I) have anti-inflammatory/antidegeneration activity as shown below in Tables II, III and IV by the effective inhibition of the proteolytic function of human granulocyte elastase.

TABLE II

| $R_1$ | q | B | $IC_{50}$ |
|---|---|---|---|
| $CH_3COO$ | 1 | $OCH_2C_6H_5(OBZ)$ | 5 |
| " | 2 | " | 0.2 |
| " | 0 | " | 10 |
| (BZ)COO | 0 | " | 20 |
| " | 2 | " | 4 |
| $C_6H_5OCH_2COO$ | 0 | " | 20 |
| " | 1 | " | 5 |
| $p\text{-}CH_3\text{—}C_6H_4\text{—}SO_2\text{—}O(TsO)$ | 1 | " | 2 |
| " | 2 | " | 0.05 |
| $6\alpha\text{-}CF_3CONH$ | 0 | " | 4 |
| " | 2 | " | 0.15 |
| $6\alpha\text{-}CF_3CON(CH_3)\text{—}$ | 0 | " | 3 |
| " | 1 | " | 3 |
| " | 2 | " | 0.2 |
| $6\beta\text{-}CF_3CONH\text{—}$ | 0 | OBZ | 12 |
| " | 2 | " | 2 |
| " | 2 | Ph | 1 |
| $6\alpha\text{-}OCH_3$ | 2 | BZ | 2 |
| " | 2 | OBZ(p-COOH) | 2 |
| $6\alpha\text{-}OC_2H_5$ | 2 | OBZ | 2 |
| " | 2 | OBZ(p-COOH) | 0.6 |
| $6\alpha\text{-}OBZ$ | 2 | OBZ | 4 |
| $6\alpha\text{-}OCH_3$ | 2 | $OCH_3$ | 20 |
| " | 2 | OBZ | 2 |

TABLE II-continued

[Structure: β-lactam with R¹ at position 6, S(O)q substituent, gem-dimethyl, and COB group]

| R₁ | q | B | IC$_{50}$ |
|---|---|---|---|
| " | 2 | OCH$_2$COOt—Bu | 3 |
| " | 2 | OCH$_2$CF$_3$ | 4 |
| 6α-CF$_3$CONH— | 2 | OCH$_2$CF$_3$ | 0.1 |
| 6α-CH$_3$CH(OH)— | 0 | OBZ | 20 |
| 6α-CH$_3$CH—<br>\|<br>OCO$_2$CH$_2$(p-NO$_2$—C$_6$H$_4$) | 2 | " | 0.2 |
| 6α-CH$_3$CH—<br>\|<br>O(CO)NH(BZ) | 2 | " | 0.6 |
| 6α-(R)—CH$_3$CH—<br>\|<br>O(CO)O(BZ) | 2 | " | 0.05 |
| 6α-CH$_3$CH—<br>\|<br>O(CO)N(CO)NHBZ<br>\|<br>BZ | 2 | " | 0.05 |
| 6α-CH$_2$O(CO)NH(BZ) | 0 | OBZ | 5 |
| " | 2 | " | 4 |
| 6β-CH$_2$O(CO)NH(BZ) | 0 | " | 15 |
| " | 2 | " | 0.7 |
| 6α-(TS)NH(TS=p-CH$_3$—C$_6$H$_4$—SO$_2$) | 0 | " | 0.1 |
| " | 2 | " | 0.2 |
| 6α-(TS)CH$_2$ | 1 | " | 4 |
| " | 2 | " | 0.3 |
| 6α-(TS)CH$_2$ | 2 | " | 2 |
| 6α-CF$_3$(CO)NH | 2 | OBZ—(p-COOt—Bu) | 0.1 |
| 6β-CF$_3$(CO)NH | 2 | " | 0.5 |
| 6α-CF$_3$(CO)NH | 2 | OBZ—(p-COOH) | 0.04 |
| 6β-CF$_3$(CO)NH | 2 | " | 1 |
| 6α-CF$_3$(CO)NH | 1 | " | 0.5 |
| 6α-CF$_3$(CO)NH | 2 | [pyrrolidine with COOt—Bu] | 20 |
| 6β-CF$_3$(CO)NH | 0 | N(CH$_3$)(BZ) | 0.6 |
| " | 2 | " | 2 |
| " | 2 | NH—BZ—(p-OCH$_3$) | 0.3 |
| 6α-CF$_3$(CO)NH | " | [pyrrolidine with COOH] | |
| " | 2 | N(CH$_3$)BZ—(p-COOt—Bu) | 0.7 |
| " | " | N(CH$_3$)BZ—(p-COOH) | 0.7 |
| 6β-CF$_3$(CO)NH | 1 | CH$_2$OCH$_3$ | 1 |
| " | 2 | " | 1 |
| 6α-CF$_3$(CO)NH | 2 | N(CH$_3$)(CH$_2$COOH) | 5 |
| " | 2 | N(CH$_3$)(CH$_2$COOt—Bu) | 0.7 |

TABLE III

Structure: β-lactam with R₁, S(O)q, CH₃, CH₂OCOCH₃, COB substituents

| R₁ | q | B | IC$_{50}$ |
|---|---|---|---|
| α-CH₃O— | 0 | OBZ | 5 |
| " | 2 | " | 4–6 |
| " | 1 | " | 4 |

TABLE IV

Structure: β-lactam with R₁, R, S(O)q, COB substituents

| R₁ | R | q | B | IC$_{50}$ |
|---|---|---|---|---|
| β-CF₃CONH— | α-CH₃O | 2 | OBZ | 9 |
| α-CF₃CONH— | β-CH₃O | 2 | " | 0.8 |
| β-CF₃CON(CH₃)— | α-C₂H₅ | 1 | " | 20 |
| β-CF₃CONH | " | 1 | " | 5 |
| " | " | 2 | " | 3 |

PROTOCOL

Enzyme assay for the Inhibition of Human
Polymorphonuclear Leukocyte Elastase Via
Hydrolysis of
N-t-Boc-alanyl-alanyl-prolylalanine-p-nitroanilide Reagents:
0.05M TES (N-tris[hydroxymethyl]methyl-2-aminoethanesulfonic acid) buffer, pH 7.5.
0.2 mM N-t-Boc-alanyl-alanyl-prolyl-alanine-p-nitroanilide (Boc-AAPAN).

To prepare substrate, the solid (m.w. 550) was first dissolved in 10.0 ml DMSO. Buffer at pH 7.5 was then added to a final volume of 100 ml.

Crude extract of human polymorphonuclear leukocytes (PMN) containing elastase activity.

Inhibitors (cephalosporin sulfoxide esters) to be tested dissolved in DMSO just before use.

Assay Procedure:
To 1.0 ml of 0.2 mM Boc-AAPAN in a cuvette, 0.01–0.1 ml of DMSO with or without inhibitor was added. After mixing, a measurement was taken at 410 mμ to detect any spontaneous hydrolysis due to of test compound. 0.05 Milliliters of PMN extract was then added and the αOD/minute at 410 mμ was measured and recorded. Beckman model 35 spectrophotometer was used.

Results:
Results were reported as IC$_{50}$, i.e., effect dosage in micrograms per milliliter (μg/ml) for 50% inhibition of the enzyme activity 2 minutes after zero time.

Comments:
The elastase activity in the crude PMN extract may vary from one preparation to another. A control of each new batch is run, and the volume added in the assay procedure is adjusted according to activity.

The following examples serve to illustrate the synthesis of certain compounds of the present invention.

EXAMPLE 1

Benzyl 6α-trifluoroacetamidopenicillanate

To an ice cooled solution of 0.35 g benzyl 6α-aminopenicillanate and 0.27 g pyridine in 25 ml methylene chloride was added 0.717 g trifluroacetic anhydride in one portion. When judged complete by TLC, the reaction was worked up by diluting with ethyl acetate and washing twice each with 10% aqueous acetic acid, brine, saturated sodium bicarbonate and brine. Drying (MgSO₄), filtration, removal of solvent and chromatography of the residue yielded 0.408 g (89%) of benzyl 6α-trifluoroacetamidopenicillanate as a yellow oil.

NMR(CDCl₃) δ 1.37(s,3H); 1.57(s,3H); 4.47(s,1H); 5.13(m,3H); 5.20(d,J=1.5 Hz,1H); 7.32(s,5H); 8.05(bd,J=8.5 Hz,1H).

EXAMPLE 2

Benzyl 6α-trifluoroacetamidopenicillanate-1,1-dioxide

To an ice cooled solution of 89.7 mgs of the above sulfide in 10 ml of methylene chloride was added 99.6 mgs of 85% m-chloroperoxybenzoic acid (m-CPBA) in one portion. The reaction was allowed to come to room temperature with stirring overnight. When judged complete by TLC, the reaction was worked up by diluting with ethyl acetate and washing successively with saturated sodium sulfite, saturated sodium bicarbonate, and saturated sodium chloride solutions. Drying (MgSO₄), filtering, removal of solvent and chromatography of the residue gave 82.1 mgs of benzyl 6α-trifluoroacetamidopenicillin-1,1-dioxide as a white foam.

NMR(CDCl₃): δ 1.26(s,3H); 1.52(s,3H); 4.38(s,1H); 4.78(d,J=1.8,1H); 5.13(AB-q,J=12.2 Hz,2H); 5.28(dd,J=7.5,J=1.8 Hz,1H), 7.30(s,5H); 7.87(bd,J=8.1 Hz,1H).

EXAMPLE 3

Benzyl 6α-(N-methyltrifluoroacetamido)penicillanate-1,1-dioxide

To a solution containing 110.8 mgs of 6α-trifluoroacetamidopenicillin benzyl ester and 38.3 mgs of dimethyl sulfate in 5 ml of acetone was added 125 mgs of finely powdered anhydrous potassium carbonate in one portion with vigorous stirring. After approximately 18 hours at room temperature the reaction was filtered and partitioned between ethyl acetate and water. The organic phase was separated, dried (MgSO₄), filtered, concentrated and the residue chromatographed to yield 44.1 mgs of benzyl 6α-(N-methyltrifluoroacetamido)-penicillinate which was oxidized with m-CPBA as in Example 2 to give Benzyl 6α-(N-methyltrifluoroacetamido)penicillanate-1,1-dioxide.

NMR(CDCl₃): δ 1.27(s,3H); 1.53(s,3H); 3.17 (bd,J=10.2 Hz,3H); 4.37(s,1H); 4.64(d,J=1.8 Hz,1H); 5.15 (AB-q,J=11.5 Hz,2H); 5.44(d,J=1.6 Hz,1H); 7.30(s,5H).

EXAMPLE 4

Benzy 6α-ethyl-6β-fluoroacetamidopenicillanate-1,1-dioxide

Benzyl 6β-amino-6α-ethylpenicillanate was acylated with trifluoroacetic anhydride and oxidized with m-CPBA as described in Example 1 and 2 to give benzyl 6α-ethyl-6β-trifluoroacetamidopenicillanate-1,1-dioxide.

NMR(CDCl$_3$): δ 1.07(t,J=7 Hz,3H); 1.23(s,3H); 1.50(s,3H); 2.21(q,J=7 Hz,2H); 4.46(s,1H); 4.64(s,1H); 5.17(ABq,J=12 Hz,2H); 7.34(s,5H); 7.58(bs,1H).

EXAMPLE 5

Benzyl 6α-ethyl-6β-(N-methyltrifluoroacetamido)penicillanate-1,1-dioxide

Alkylation of benzyl 6α-ethyl-6β-trifluoroacetamidopenicillanate with potassium carbonate/dimethyl sulfate as described in Example 3, followed by m-CPBA oxidation of the resulting N-methyltrifluoroacetamide as in Example 2 gave benzyl 6α-ethyl-6β-(N-methyltrifluoroacetamido)penicillanate-1,1-dioxide.

NMR(CDCl$_3$): δ 1.09(t,J=8 Hz,3H); 1.23(s,3H); 1.50(s,3H); 2.18(q,J=8 Hz,2H); 3.26(m,3H); 4.43(s,1H); 4.68(s,1H); 5.16(ABq,J=12 Hz,2H); 7.33(s,5H).

EXAMPLE 6

Benzyl 6α-acetamido-6β-methoxypenicillanate-1,1-dioxide and Benzyl 6β-acetamido-6α-methoxypenicillanate-1,1-dioxide A solution of 99.5 mgs of benzyl 6β-trifluoroacetamidopenicillanate in 5 mls dry THF was cooled in a dry ice/acetone bath and treated with 32.9 mgs of solid lithium methoxide followed 1 minute later with 29.8 μl of 8.29M t-butyl hypochlorite in THF. After another 15 min at −70° C., the reaction was quenched by pouring into aqueous acetic acid solution. Extraction with ethyl acetate followed by sequential washing of the organic phase with water, saturated sodium bicarbonate solution and water gave a solution which was dried (MgSO$_4$), filtered, concentrated and chromatographed to yield 21.5 mgs of an epimeric mixture of sulfides. Oxidation of the mixture using m-CPBA in CH$_2$Cl$_2$ was carried out as in Example 2 to give 7.6 mgs of the corresponding sulfones. Separation of the two isomers was achieved using preparative TLC with 96.5: 3.5 CH$_2$Cl$_2$:EtOAc as the mobile phase to give 4.2 mgs benzyl 6α-acetamido-6β-methoxypenicillanate-1,1-dioxide (R$_f$ range=0.41–0.49); and 3.2 mgs benzyl 6β-acetamido-6α-methoxypenicillanate-1-dioxide (R$_f$ 0.30–0.41).

EXAMPLE 7

Benzyl 6α-ethoxypenicillinate

A well stirred ice cold mixture of 5.0 gms of the p-toluenesulfonic acid salt of benzyl 6β-aminopenicillanate, 110 ml methylene chloride, 110 ml water, and 13.2 g sodium nitrite was treated with 2.0 g of p-toluenesulfonic acid monohydrate (TSOH·H$_2$O) in portions over 10 min. The mixture was allowed to stir another 15 minutes, at which time the yellow organic phase was separated and washed with cold brine, dried (MgSO$_4$) and filtered into an ice cold solution of 1.90 g TSOH·H$_2$O in 50 ml of absolute ethanol. After 20 minutes, this mixture was diluted with ethyl acetate and washed with saturated sodium bicarbonate and saturated sodium chloride solutions, dried (Na$_2$SO$_4$), filtered, concentrated and the residue chromatographed to give 0.685 g of benzyl 6α-ethoxypenicillanate as a yellow oil (20% yield). NMR(CDCl$_3$): δ 1.24(t,J=8Hz,3H); 1.38(s,3H); 1.53(s,3H); 3.65(q,J=8 Hz,2H); 4.45(s,1H); 4.53(d,J=1.35 Hz,1H); 5.14(s,2H); 5.22(d,J=1.35 Hz,1H); 7.32(s,5H).

EXAMPLE 8

Benzyl 6α-ethoxypenicillantate-1,1-dioxide

Oxidation of 0.685 g of benzyl 6α-ethoxypenicillanate in 20 ml CH$_2$Cl$_2$ wtih 0.912 g of 85% m-CPBA give 0.4988 g of Benzyl 6α-ethoxypenicillanate-1,1-dioxide as yellow oil after chromatography (67% yield). NMR(CDCl$_3$): δ 1.19(t,J=7 Hz,3H); 1.25(s,3H); 1.50(s,3H); 3.68(dq,J=7.0,1.1 Hz, 2H); 4.35(s,1H); 4.53(d,J=1.4 Hz,1H); 4.93(d,J=1.4 Hz,1H); 5.13(ABq,J=11.5 Hz,2H); 7.32(s,5H).

EXAMPLE 9

(4-Carbomethoxy)benzyl 6α-methoxypenicillanate-1,1-dioxide

A slurry containing 202.4 mgs 6-aminopenicillanic acid (6-APA) and 94.7 mgs triethylamine in 4 ml of acetone was treated dropwise with a solution of 67.3 mgs of 4-carbomethoxybenzyl bromide in 1 ml of acetone. After stirring 3 days at room temperature the reaction was diluted with ethyl acetate and washed with saturated sodium bicarbonate solution and water. Drying (MgSO$_4$), filtration and removal of solvent yielded 93.5 mgs (78%) of a crude yellow oil which was used without further purification in the subsequent diazotization (see Example 5) and oxidation (see Example 2) steps to give (4-carbomethoxy)benzyl 6α-methoxypenicillanate-1,1,-dioxide.

NMR(CDCl$_3$): δ 1.30(s,3H); 1.52(s,3H); 3.55(s,3H); 3.92(s,3H); 4.37(s,1H); 4.53(d,J=1.5 Hz,1H); 4.95(d,J=1.5 Hz,1H); 5.22(ABq,2H); 7.38(d,J=8 Hz,2H); 8.02(d,J=8 Hz,2H).

EXAMPLE 10

Benzyl 6α-acetoxypenicillanate-1,1-dioxide

A solution containing 253 mgs of benzyl 6α-hydroxypenicillanate and 98 mgs of pyridine was treated with 97 mgs of acetyl chloride at 0° C. TLC indicated that the reaction was complete after 30 min. It was diluted with ethyl acetate and washed three times with 10% aqueous acetic acid, brine, saturated sodium bicarbonate solution and once again brine. Drying (MgSO$_4$), filtration, removal of solvent and chromatography of the residue gave 265 mgs (92%) of the desired sulfide as a colorless oil. Oxidation of the sulfide with m-CPBA was carried out as in Example 2 to give benzyl 6α-acetoxypenicillanate-1,1-dioxide.

NMR(CDCl$_3$): δ 1.27(s,3H); 1.53(s,3H); 2.15(s,3H); 4.38(s,1H); 4.58(d,J−1.4 Hz,1H); 5.18(ABq,J=11.7 Hz,2H); 5.85(d,J=1.4Hz,1H); 7.35(s,5H).

EXAMPLE 11

Benzyl 6β-[(R)-1'-(benzyloxycarbonyloxy)ethyl]-penicillanate-1-dioxide

A solution containing 6.8 mgs of benzyl 6β-[(R)-1'-hydroxyethyl]penicillanate and 5.0 mgs of dimethylaminopyridine (DMAP) dissolved in 0.3 ml CH$_2$Cl$_2$ was treated with 6.9 mgs of benzyl chloroformate at under 0° C. under $N_2$. At one hour intervals additional aliquots of benzyl chloroformate and DMAP were added until TLC indicated consumption of the starting penicillanate. The reaction was then diluted with ethyl acetate and washed successively with saturated sodium bicarbonate, water, 10% aqueous acetic acid, water, saturated sodium bicarbonate and finally water. The resulting organic phase was dried ($MgSO_4$), filtered, concentrated and the residue was chromatographed to give 6.5 mgs (68% yield) of the desired benzyl carbonate. Oxidation with m-CPBA was then carried out as described in Example 2 to give 7.2 mgs of benzyl 6β-[(R)-1'-(benzyloxycarbonyloxy)ethyl]-penicillanate-1,1-dioxide, $R_f$=0.42(TLC) on silica gel using 70:30/hexane:ethyl acetate as the eluting solvent.

Substitution of the appropriate 6-(1'-hydroxyethyl)-penicillanate in Example 11, gave the corresponding 6β-[(S)-, 6α-[(R)- and 6α[(S)-1'-(benzyl,oxycarbonyloxy)ethyl]penicillanate-1,1-dioxides.

EXAMPLE 12

Benzyl 6α-[(R)-1'-(benzylaminocarbonyloxy)ethyl]-penicillanate-1,1-dioxide

Substitution of benzyl isocyanate for benzyl chloro formate in Example 11 yields the corresponding benzyl carbamates. Thus 8.9 mgs of benzyl 6α-[(R)-1-hydroxyethyl]penicillanate gave 12.4 mgs of benzyl 6α-[(R)-1'-benzylaminocarbonyloxy)ethyl]-penicillanate which was oxidized with 11.4 mgs of 85% m-CPBA to give 6.5 mgs of Benzyl 6α-[(R)-1'-(benzylamino-carbonyloxy)ethyl]penicillanate-1,1-dioxide $R_f$0.28 (TLC) on silic gel using 70:30/hexane:ethyl acetate as the eluting solvent system.

Substitution of the appropriate 6-(1'-hydroxyethyl)-penicillanate in Example 12 gave the corresponding 6α[(S)-,6β-[(R)- and 6β-[(S)-1'-(benzylaminocarbonyloxy)ethyl]penicillanate-1,1-dioxides.

EXAMPLE 13

Benzyl 6-bromo-6-hydroxymethylpenicillanates

A solution containing 252.0 mgs of benzyl 6,6-dibromopenicillanate dissolved in 5 ml of dry THF was cooled under $N_2$ in a dry ice/acetone bath and treated dropwise with 217 μl of a 2.85M solution of methylmagnesium bromide in diethyl ether. After an additional 20 min, 100 mgs of paraformaldehyde was sublimed into the reaction flask using a heat gun and the $N_2$ flow. The reaction was maintained at −70° C. for an additional 35 min, then quenched by pouring into 10% aqueous HOAc/ethyl acetate. The organic phase was washed sequentially with water, saturated sodium bicarbonate solution and water. Drying ($MgSO_4$), filtration, removal of solvent in vacuo and chromatography of the residue gave 119.9 mgs (53%) of an epimeric mixture of benzyl 6-bromo-6-hydroxymethylpenicillanates.

NMR($CDCl_3$): δ 1.38(s,3H); 1.63(s,3H); 3.33(Br,1H); 4.05(bm,2H); 4.48(s,1H); 5.13(s,2H); 5.47(s,1H); 7.29(s,5H).

EXAMPLE 14

Benzyl 6-hydroxymethylpenicillanates

A mixture of 119.9 mgs of epimeric benzyl 6-bromo6-hydroxymethyl-penicillanates and 78.3 mgs of zinc dust in 5 ml of diethyl ether and 1.5 ml of 1M aqueous ammonium acetate was vigorously stirred for 1½ hours at room temperature. TLC indicated incomplete reaction at that time so an additional 78.3 mgs zinc dust and 1.5 ml 1M ammonium acetate was added to the reaction. After another 30 minutes at room temperature the reaction was judged complete by TLC and worked up by filtering, diluting with ether and water washing. Drying ($MgSO_4$), filtering, removal of solvent and preparative TLC (80:20/$CH_2Cl_2$:EtOAc) of the resulting residue gave 59.0 mgs (61%) of a 60:40 mixture of benzyl 6α:6β 6-hydroxymethylpenicillanate.

NMR($CDCl_3$): δ 1.41(s,1.5H); 1.38(s,1.5H); 1.61(s,3H); 2.53(br,1H); 3.44(dt,J=4.5,1.5 Hz,0.5H); 3.63–4.20(m,2.5H); 4.38(s,0.5H); 4.45(s,0.5H); 5.16(s,2H); 5.23(dJ=1.5 Hz,0.5H); 5.40(d,J=4 Hz,0.5H); 7.35(s,5H).

EXAMPLE 15

Benzyl 6-chloromethylpenicillanates 390 mgs of a mixture of epimeric benzyl 6-hydroxymethylpenicillanates and 627.5 mgs of N-ethyldiisopropylamine were combined in 18 ml methylene chloride under $N_2$, cooled in a −20° C. bath, and treated with 173.3 mgs thionyl chloride. After 20 minutes at −20° the reaction was concentrated and chromatographed to give 0.2694 g of an epimeric mixture of benzyl 6-chloromethylpenicillanates, $R_f$=3.31 on silica gel TLC plates using 70:30/hexane:ethyl acetate as the eluting solvent system.

EXAMPLE 16

Benzyl 6α-(phenylulfonyl)methylpenicillanate-1,1-dioxide

To a solution of 44.6 mgs of an epimeric mixture of benzyl 6-chloromethylpenicillanates in 6 ml dry DMF was added 20.2 mgs of solid potassium thiophenoxide in one portion with stirring at room temperature. The reaction mixture was allowed to stir 30 minutes before it was partitioned between water and ethyl acetate. The organic phase was washed twice with water, dried ($MgSO_4$), filtered concentrated and chromatographed to give 14.6 mgs of Product (27% yield) which was combined with other batches to give 98.1 mgs of material for separation by HPLC. Multiple elutions of aliquots of the combined batches on a Whatman Magnum 9(50 cm) partasil column using 75:25/$CH_2Cl_2$:Hexane as the mobile phase gave 18.7 mgs of the benzyl 6β-(phenylthiomethyl)penicillanate and 61.1 mgs of its 6α-isomer.

Oxidation of 21.8 mgs of the above 6α-isomer with 47.1 mgs of 85% m-CPBA as described in Example 2 gave 23.2 mgs (92% yield) of Benzyl 6α-(phenylsulfonyl)methylpenicillanate-1,1-dioxide.

NMR($CDCl_3$): δ 1.27(s,3H); 1.52(s,3H); 3.43–4.17(m,3H); 4.27(s,1H); 4.65(d,J=1.4 Hz,1H); 5.11(Abq,J=11.9 Hz,2H); 7.27(s,5H); 7.33–7.93(m,5H).

EXAMPLE 17

Benzyl 6α-methoxypenicillanate-1-oxide

A solution of 0.7088 gm of 85% m-CPBA in $CH_2Cl_2$ was added rapidly to an ice cold solution of 1.122 g of benzyl 6α-methoxypenicillanate in $CH_2Cl_2$ under nitrogen. A TLC of the reaction mixture immediately following the addition showed no starting material. The cold reaction was quenched into 50 ml of a saturated sodium sulfite solution. The resulting mixture was then extracted with ethyl acetate and the organic phase was washed thoroughly with saturated sodium sulfite, saturated sodium bicarbonate and brine solutions. Drying (MgSO₄), filtration and removal of solvent gave 1.164 gms of crude benzyl 6α-methoxypenicilllanate-1-oxide NMR(CDCl₃); δ 1.0(s,3H); 1.60(s,3H); 3.53(s,3H); 4.43(s,1H); 4.85(m,2H); 5.15(ABq,2H); 7.32(s,5H).

EXAMPLE 18

Benzyl 2α-acetoxymethyl-6α-methoxy-2β-methylpenam-3α-carboxylate-1,1-dioxide and Benzyl 2β-acetoxymethyl-6α-methoxy-2α-methylpenam-3α-carboxylate-1,1-dioxide 105.5 mgs of benzyl 6α-methoxypenicillanate-1-oxide in 15 ml of acetic anhydride was placed under a nitrogen atmosphere and heated for 2.25 hrs in a 120° C. oil bath. The reaction was then quenched by pouring into excess methanol/saturated aqueous sodium bicarbonate. Addition of water and ethyl acetate resulted in a two phase system which was then separated. The organic phase was washed with water, dried (MgSO₄), filtered, concentrated in vacuo and chromatographed to give 35.2 mgs of a mixture of epimeric benzyl 2-acetoxymethyl-6α-methoxy-2-methylpenam-3α-carboxylates. Separation of the two epimers was carried out on an analytical HPLC equipped with a Whatman Magnum 9 (50 cm) partisil column. Obtained were: 10.0 mgs of the β-acetoxymethyl epimer and 19.1 mgs of the α-acetoxymethyl epimer. Oxidation of the individual isomers to the corresponding sulfone was then carried out using m-CPBA in CH₂Cl₂ as described in Example 2 to yield:

(a) Benzyl 2α-acetoxymethyl-6α-methoxy-2βmethylpenam-3α-carboxylate-b 1,1-dioxide (CDCl₃): δ 1.29(s 3H) 2.05(s,3H); 3.53(s,3H); 4.32(ABq,2H); 4.53(d,J=1.5 Hz,1H); 4.61(s,1H); 4.94(d,J=1.5 Hz,1H) 5.20(s,2H); 7.35(s,5H).

(b) Benzyl 2β-acetoxymethyl-6α-methoxy-2β-methylpenam-3α-carboxylate-1,1-dioxide NMR (CDCl₃): δ 1.47(s,3H); 2.00(s,3H); 3.47(s,3H); 4.22(ABq,2H); 4.55(bs,1H); 4.82(S,1H); 5.05(S,1H); 5.15(ABq,2H); 7.30(s,5H).

EXAMPLE 19

2-Dimethyl-6β-(triphenylmethylamino)-3-(N-methyl-N-benzylcarbamoyl)penam

To a suspension of 6-aminopenicillanic acid (30.6 g) in chloroform (150 mL) was added triethylamine (27.8 mL). The mixture was stirred at room temperature until almost completely in solution at which time trityl chloride (21.7 g) was added in one portion. The reaction was stirred at room temperature for 60 hrs to give a solution of triethylammonium 2,2-dimethyl-6β-(triphenylmethylamino)penicillanate.

A 40 mL portion of the above solution was cooled to 0° C. in an ice bath and additional triethylamine (2.8 mL) was added. Ethyl chloroformate (2.0 mL) was then added and after ½ hour N-methylbenzylamine (5 mL) was added via pipette below the surface of the reaction. After ½ hour further stirring at room temperature, was poured into water and extracted with methylene chloride (2×). The extracts were washed with dilute hydrochloric acid, sodium bicarbonate solution and brine, dried over sodium sulfate and evaporated. The residue was flash chromatographed using a solvent gradient of 20 to 30% ethyl acetate/hexane to give 2.2 g of 2,2-dimethyl-6β-(triphenylmethylamino)-3-(N-methyl-N-benzylcarbamoyl)penam NMR (CDCl₃): δ 1.33(s,3H), 1.60(s,3H), 2.87(2 close s,3H), 3.33(br d,1H,10 Hz), 4.3-4.7(m,4H), 4.80(2 close s,1H), 7.0-7.8(m,20H).

EXAMPLE 20

6-Amino-2,2-dimethyl-3-(N-methyl-N-benzylcarbamoyl)pena m p-toluenesulfonic acid salt To a solution of 2,2-dimethyl-6-(triphenylmethylamino)-3-(N-methyl-N-benzylcarbamoyl)penam (200 mg) in acetone (2 mL) was added p-toluenesulfonic acid monohydrate (70 mg). The solution was stirred at room temperature for 1½ hours and the acetone was removed in vacuo. Trituration of the residue with ether and vacuum drying gave partially impure 6-Amino-2,2-dimethyl-3-(N-methyl-N-benzylcarbamoyl)penam p-toluenesulfonic acid salt (200 mg).

EXAMPLE 21

2-Dimethyl-6-(trifluoroacetamido)-3-(N-methyl-N-benzyl-carbamoyl)penam

To a solution of 6-amino-2,2-dimethyl-6-(N-methyl-N-benzylcarbomoyl)penam p-toluenesulfonic acid salt (200 mg) in methylene chloride (5 mL) at 0° C. was added pyridine (100 μL) followed by trifluoroaceticanhydride (86 μL). After 20 min. the reaction was poured into cold sodium bicarbonate solution and extracted with methylene chloride (2×). The extracts were washed with brine, dried over and Na₂SO₄ and evaporated. The residue was purified by flash chromatography (30–40% EtOAc/hexane) to give 2,2-diimethyl-6-(trifluoroacetamido)-3-(N-methyl-N-benzylcarbamoyl)penam.

NMR (CDCl₃): δ 1.53(s,3H), 1.61(s,3H), 2.96(s,3H), 4.54(ABq,2H), 4.89(s,1H), 5.50(dd,1H,J=4 Hz, J=9 Hz), 5.80(d,1H,J=4 Hz), 7.4(br.s,5H).

EXAMPLE 22

2-Dimethyl-6-(trifluoroacetamido)-3-(N-methyl-N-benzylcarbamoyl)penam-1,1-dioxide The oxidation of 2,2-dimethyl-6-(trifluoromethylcarboxamido)-3-(N-methyl-N-benzylcarbamoyl)penam to give 2,2-Dimethyl-6-(trifluoro-acetamido)-3-(N-methyl-N-benzylcarbamoyl)penam-1,1-dioxide was carried out as above.

NMR (CDCl₃): δ (mixture of cis and trans amides at C-3) 1.3–1.5(3s,6H), 3.0(2s,3H), 4.51(ABq,2H), 4.89(d,1H,J=4.5 Hz), 5.05(s,1H), 5.62(dd,1H,J=4.5 Hz,J-10 Hz), 7.0–7.3(m,5H), 7.90 (bd,1H,J=10 Hz).

What is claimed is:

1. A method of treating or managing elastase-mediated conditions comprising the administration to a patient in need of such treatment an effective amount of a compound of structural formula:

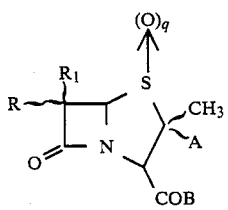

wherein:

q is 0, 1 or 2:
A is
(a) CH₂OCOR$_a$ where R$_a$ represents H or C$_{1-6}$alkyl;
(b) —CH₃;
(c) CH₂OR$_a$;
(d) CH₂Cl; or
(e) hydrogen;
R₁ is (1) R'NR$_a$ wherein R$_a$ is H or C$_{1-6}$ alkyl and R' is
(a) hydrogen;
(b) CF₃CO;
(c) CF₃OCO;
R₂SO₂ wherein R₂ is phenyl, benzyl, H, C$_{1-6}$ alkyl or CF₃ wherein the phenyl and the benzyl may optionally be substituted with one or more of a substituent selected from a group consisting of hydroxy, halo, nitro, amino, carboxy, thio, C$_{1-6}$alkyl and CF₃;
(e) R₂CO;
(f) R₂O(CO);
(g) (R₂O)₂P(O)—;
(h) R₂;
(i) R₂(C=S)—;
(2) C$_{1-6}$alkoxycarbonyloxyC$_{1-6}$alkyl;
(3) benzoxycarbonyloxyC$_{1-6}$alkyl;
(4) hydroxyC$_{1-6}$alkyl;
(5) OR$_1$' where R$_1$' is
(a) C$_{1-6}$alkyl;
(b) phenyl as previously defined;
(c) benzyl as previously defined;
(d) —COR'₂ wherein R'₂ represents H, R₂, or C$_{1-6}$alkylamino;
(e) COOR₂; or
(f) R₂SO₂—;
(6) SR$_1$';
(7) hydrogen;
(8) C$_{1-6}$alkyl;
(9) C$_{1-6}$ alkoxycarbonyl C$_{1-6}$ alkyl;
(10) phenoxycarbonyloxy C$_{1-6}$ alkyl;
(11) benzylaminocarbonyloxyC$_{1-6}$alkyl;
(12) R'NCF₃;
(13) OH;
(14) CN;
(15) halo;
(16) —O(CO)CH₂OR₂;
(17) —COOR₂;
(18) —CH₂SR₂ or —CH₂SO₂R₂;
(19) phthalimido;
(20) R₂SO₂;
(21) —CH₂ OR'₃ or CH₃CH(OR'₃) wherein R'₃ is R₂, —COOR₂, —(OC)R₂, —CONHR₂, or —(CO)NR₂(CO)NHR₂;
(22) benzyl as previously defined;
B is OB₁ or NB₂B₃ wherein B₁ and B₂ independently are:
(1) straight or branched chain alkyl having from 1 to 6 carbon atoms;
(2) aryl having from 6 to 19 carbon atoms;
(3) cycloalkyl having from 3 to 8 carbon atoms;
(4) alkenyl having from 2 to 20 carbon atoms;
(5) cycloalkenyl having from 5 to 8 carbon atoms;
(6) alkynyl having from 2 to 20 carbon atoms;
(7) aralkyl, alkaryl, aralkenyl, aralkynyl, alkenylaryl or alkynylaryl wherein alkyl, aryl, alkenyl and alkynyl are as previously defined;
(8) C$_{1-6}$ alkenyl C$_{1-6}$ alkyl;
(9) C$_{1-6}$ alkenoyl C$_{1-6}$ alkyl;
(10) C$_{1-6}$ alkanoyloxy C$_{1-6}$ alkyl;
(11) C$_{1-6}$ alkanoyl;
(12) a heterocyclic group including heterocyclic alkyl or heterocyclic alkenyl;
(13) benzoxycarbonyl;
(14) —CH₂COOH;
(15) —CH₂COOC$_{1-6}$alkyl;
(16) —CH₂COObenzyl;
the above groups (1)-(12) being unsubstituted or substituted with one or two radicals selected from a group consisting of alkyl, hydroxy, alkoxy, halo, nitro, mercapto, amino, monoalkylamino or dialkylamino, cyano, carboxy, sulfoamino, carbamoyl, carbamoyloxy, alkyl- or amino-sulfonyl, alkyl- or amino-sulfinyl, sulfamoyl, azido, carboxamido or N-alkyl carboxamido;
B₃ is B₁ or hydrogen;
B₂ and B₃ may join together and form part of the heterocyclic group

which represents

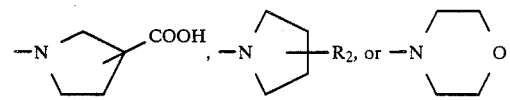

wherein R₂ is as previously defined; and
R is
(a) H;
(b) halo;
(c) OR₂; or
(d) C$_{1-6}$alkyl.

2. The method of claim 1 wherein
q is 2;
A is CH₃ or CH₂O(CO)CH₃;
R₁ is
(1) R'NR$_a$ where R$_a$ is H or C$_{1-3}$ alkyl and R, represents:
(a) CH₃CO—;
(b) CF₃CO—;
(c) HCO—;
(d) methoxycarbonyl; or
(e) (p—CH₃—C₆H₄)SO₂—;
(2) R'NCF₃—;
(3) C$_{1-3}$alkyl;
(4) CH₂C₆H₅;
(5) OR$_1$' where R$_1$'is
(a) C$_{1-6}$ alkyl;
(b) —C₆H₅;
(c) —CH₂C₆H₅; or
(d)

where R₂', represents R₂ as previously defined, or C$_{1-6}$alkylamino; or
(e) (p—CH₃—C₆H₄)—SO₂—;
(6) Cl or F;
(7) —SO₂R₂ wherein R₂ is benzyl or C$_{1-3}$ alkyl;

(8) CH$_2$OR$_3'$ or CH$_3$CH(OR$_3'$) wherein R$_3$, is —COOCH$_2$C$_6$H$_5$, —(OC)OCH$_2$— (p—NO$_2$—C$_6$H$_4$), —CONHCH$_2$C$_6$H$_5$ or —CON(CH$_2$C$_6$H$_5$)(CO)NHCH$_2$C$_6$H$_5$;

(9) H;

(10)

—OCCH$_2$OR$_2$;

(11)

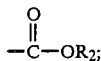
—C—OR$_2$;

(12)

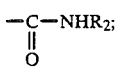
—C—NHR$_2$;

(13) —CH$_2$SO$_2$R$_2$; or
(14) —CH$_2$SR$_2$.

R is
  (a) H;
  (b) CH$_3$ or C$_2$H$_5$; or
  (c) OCH$_3$; and

B is OB$_1$ or NB$_2$B$_3$ wherein B$_1$ and B$_2$ independently are
(1) benzyl as previously defined;
(2) C$_{1-4}$alkyl;
(3) CH$_2$COOC$_{1-4}$ alkyl;
(4) —CH$_2$COOH
(5) —CH2COObenzyl;
(6) C$_{1-6}$ alkanoyloxymethyl;
(7) C$_{1-6}$ alkanoylmethyl
(8) halo C$_{1-4}$ alkyl; or
(9) benzoxycarbonyl;

B$_3$ is B$_1$ or H; and

B$_2$ and B$_3$ may join together and form part of the heterocyclic group selected from a group consisting of

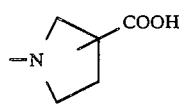  and

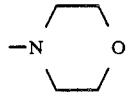

wherein R$_2$ is as previously defined.

3. The method of claim 1 wherein the active compound is selected from a group consisting of compounds as defined in the following table:

[Structure showing: R—, R$_1$, S(O)$_q$, CH$_3$, A, N, COB]

| R$_1$ | q | B |
|---|---|---|
| CH$_3$COO | 1 | OCH$_2$C$_6$H$_5$(OBZ) |
| " | 2 | " |
| " | 0 | " |
| (BZ)COO | 0 | " |
| " | 2 | " |
| C$_6$H$_5$OCH$_2$COO | 1 | " |
| " | 1 | " |
| P—CH$_3$—C$_6$H$_4$—SO$_2$—O(TsO) | 1 | " |
| " | 2 | " |
| 6α-CF$_3$CONH | 0 | " |
| " | 2 | " |
| 6α-CF$_3$CON(CH$_3$)— | 0 | " |
| " | 1 | " |
| " | 2 | " |
| 6β-CF$_3$CONH— | 0 | OBZ |
| " | 2 | " |
| " | 2 | Oph |
| 6α-OCH$_3$ | 2 | OBZ |
| " | 2 | OBZ(p-COOH) |
| 6α-OC$_2$H$_5$ | 2 | OBZ |
| " | 2 | OBZ(p-COOH) |
| 6α-OBZ | 2 | OBZ |
| 6α-OCH$_3$ | 2 | OCH$_3$ |
| " | 2 | OBZ |
| " | 2 | OCH$_2$COOt-Bu |
| " | 2 | OCH$_2$CF$_3$ |
| 6α-CF$_3$CONH— | 2 | OCH$_2$CF$_3$ |
| 6α-CH$_3$CH(OH)— | 0 | OBZ |

-continued

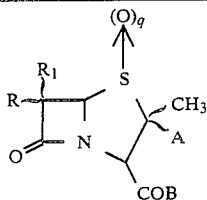

| R₁ | q | B |
|---|---|---|
| 6α-CH₃CH— <br>     \| <br> OCO₂CH₂(P—NO₂—C₆H₄) | 2 | " |
| 6α-CH₃CH— <br>     \| <br> O(CO)NH(BZ) | 2 | " |
| 6α-(R)—CH₃CH— <br>     \| <br> O(CO)O(BZ) | 2 | " |
| 6α-CH₃CH— <br>     \| <br> O(CO)N(CO)NHBZ <br>     BZ | 2 | " |
| 6α-CH₂O(CO)NH(BZ) | 0 | OBZ |
| " | 2 | " |
| 6β-CH₂O(CO)NH(BZ) | 0 | " |
| " | 2 | " |
| 6α-(TS)NH(TS=p-CH₃—C₆H₄—SO₂) | 0 | " |
| " | 2 | " |
| 6α-(TS)CH₂ | 1 | " |
| " | 2 | " |
| 6β-(TS)CH₂ | 2 | " |
| 6α-CF₃(CO)NH | 2 | OBZ—(p-COOT-Bu) |
| 6β-CF₃(CO)NH | 2 | OBZ-(p-COOt-Bu) |
| 6α-CF₃(CO)NH | 2 | OBZ-(p-COOH) |
| 6β-CF₃(CO)NH | 2 | OBZ-(p-COOH) |
| 6α-CF₃(CO)NH | 1 | OBZ-(p-COOH) |
| 6α-CF₃(CO)NH | 2 | OBZ-)p-COOH) |
| 6β-CF₃(CO)NH | 0 | [(CO)]N(CH₃)(BZ) |
| 6β-CF₃(CO)NH | 2 | [(CO)]N(CH₃)(BZ) |
| 6β-CF₃(CO)NH | 2 | [(CO)]NH—BZ—(p-OCH₃) |
| 6β-CF₃(CO)NH | 0 | NH(CO)OBZ |
| 6β-CF₃(CO)NH | 2 | NH(CO)OBZ |
| 6β-CF₃(CO)NH | 1 | [(CO)]CH₂OCH₃ |
| 6β-CF₃(CO)NH | 2 | [(CO)]CH₂OCH₃ |
| 6α-CF₃(CO)NH | 2 | [(CO)]N(CH₃)(CH₂COOH) |
| 6α-CF₃(CO)NH | 2 | [(CO)]N(CH₃)(CH₂COOt-Bu) |

4. The method of claim 1 wherein the active compound is selected from a group consisting of compounds as defined in the following table:

| R₁ | q | B |
|---|---|---|
| α-CH₃O— | 0 | OBZ |
| " | 2 | " |
| " | 1 | " |

5. The method of claim 1 wherein the active compound is selected from a group consisting of compounds as defined in the following table:

| R₁ | R | q | B |
|---|---|---|---|
| β-CF₃CONH— | α-CH₃O | 2 | OBZ |
| α-CF₃CONH— | β-CH₃O | 2 | " |
| β-CF₃CON(CH₃)— | α-C₂H₅ | 1 | " |
| " | " | | |
| β-CF₃CONH | " | 1 | " |
| " | " | 2 | " |

6. The method of claim 1 wherein the compound is

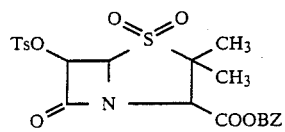
wherein B2 represents benzyl and Ts represents tosyl.
7. The method of claim 1 wherein the compound is
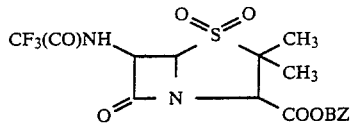
wherein Bs represents benzyl.
8. The method of claim 1 wherein the compound is
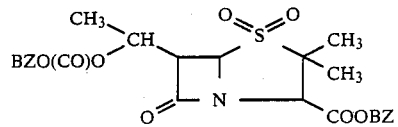
wherein BZ represents benzyl.
9. The method of claim 1 wherein the compound is
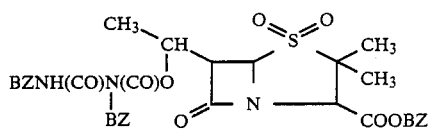
wherein I is benzyl.
* * * * *